(12) United States Patent
Barmaimon et al.

(10) Patent No.: US 11,311,670 B2
(45) Date of Patent: Apr. 26, 2022

(54) AUTOMATIC INJECTION DEVICE HAVING A PASSIVE DRIVE SYSTEM WITH A SHAPE MEMORY SPRING

(71) Applicant: FLEX LTD., Singapore (SG)

(72) Inventors: Eyal Barmaimon, Haifa (IL); Lior Shtram, Tel Aviv (IL); Nadav Cohen, Haifa (IL)

(73) Assignee: FLEX LTD, Singapore (SG)

( * ) Notice: Subject to any disclaimer, the term of this patent is extended or adjusted under 35 U.S.C. 154(b) by 139 days.

(21) Appl. No.: 16/159,571

(22) Filed: Oct. 12, 2018

(65) Prior Publication Data

US 2020/0114080 A1  Apr. 16, 2020

(51) Int. Cl.
| | | |
|---|---|---|
| *A61M 5/20* | (2006.01) | |
| *A61M 5/145* | (2006.01) | |
| *A61M 5/44* | (2006.01) | |
| A61M 5/31 | (2006.01) | |
| A61M 5/315 | (2006.01) | |
| F16F 1/32 | (2006.01) | |

(52) U.S. Cl.
CPC ............ *A61M 5/20* (2013.01); *A61M 5/1454* (2013.01); *A61M 5/44* (2013.01); *A61M 5/2033* (2013.01); *A61M 5/31576* (2013.01); *A61M 2005/3115* (2013.01); *A61M 2205/0266* (2013.01); *A61M 2205/0272* (2013.01); *F16F 1/326* (2013.01)

(58) Field of Classification Search
CPC ............ A61M 5/20; A61M 2005/2006; A61M 5/2033; A61M 2005/2073; A61M 5/1454; A61M 2005/14506; A61M 2005/3115; A61M 5/31565; A61M 5/31571; A61M 5/31576; A61M 2005/202; F16F 1/324; F16F 1/326
See application file for complete search history.

(56) References Cited

U.S. PATENT DOCUMENTS

| | | | | |
|---|---|---|---|---|
| 5,178,609 A | * | 1/1993 | Ishikawa | A61M 5/1454 |
| | | | | 128/DIG. 12 |
| 6,371,464 B1 | * | 4/2002 | Porche | F16F 1/08 |
| | | | | 267/166.1 |

(Continued)

FOREIGN PATENT DOCUMENTS

| | | |
|---|---|---|
| WO | 2004/000395 A1 | 12/2003 |
| WO | 2014/162466 A1 | 10/2014 |
| WO | 2017177094 A2 | 10/2017 |

OTHER PUBLICATIONS

International Search Report dated Dec. 10, 2019 for PCT Application No. PCT/IB2019/058708 filed on Oct. 11, 2019.

(Continued)

*Primary Examiner* — Nilay J Shah
(74) *Attorney, Agent, or Firm* — Volpe Koenig (57) ABSTRACT

An automatic injection device has an insertion needle configured to be inserted into a patient and a drug container which contains a pharmaceutical product and includes a plunger. The automatic injection device also has a fluid path which fluidly connects the drug container to the insertion needle, and a drive system configured to cause linear movement of the plunger to force the pharmaceutical product into the fluid path. The passive drive system has a movable element. The movable element has a shape memory alloy and is configured to change shape to move the plunger.

19 Claims, 7 Drawing Sheets

(56) References Cited

U.S. PATENT DOCUMENTS

| | | | |
|---|---|---|---|
| 7,959,715 B2 | 6/2011 | Kavazov et al. | |
| 8,172,811 B2 | 5/2012 | Roe | |
| 2003/0229310 A1* | 12/2003 | Flaherty | A61M 5/1452 604/151 |
| 2005/0055014 A1 | 3/2005 | Coppeta et al. | |
| 2007/0112326 A1* | 5/2007 | Bosshard | A61M 5/145 604/500 |
| 2016/0146282 A1* | 5/2016 | Collard | F16F 3/12 267/140.4 |
| 2017/0290975 A1 | 10/2017 | Barmaimon et al. | |
| 2019/0022306 A1 | 1/2019 | Gibson et al. | |

OTHER PUBLICATIONS

International Search Report for WO Application PCT/US2017/018478 dated Apr. 21, 2017.

* cited by examiner

Before Heat Treatment

FIG. 8C

After Heat Treatment

FIG. 8E

After Heat Treatment Compressed

AUTOMATIC INJECTION DEVICE HAVING A PASSIVE DRIVE SYSTEM WITH A SHAPE MEMORY SPRING

FIELD OF INVENTION

The present disclosure relates to an automatic injection device, and, in particular, to an automatic injection system having a passive drive system with a shape memory spring.

BACKGROUND

Injection devices are used to deliver pharmaceutical products such as biologics and medications to a patient (i.e., a person or animal). A syringe and needle is an example of a widely-used injection device. This basic system typically involves a person manually moving a plunger portion of the syringe to force the pharmaceutical product through the needle and into the patient. Other injection devices have been developed to deliver pharmaceutical products automatically at the touch of a button or the actuation of a switch. These devices are advantageous in that they allow a patient to more easily self-administer the pharmaceutical product. Moreover, some automatic injection devices allow for slow or periodic delivery of the pharmaceutical product as needed, which is typical procedure for patients dependent on insulin injections, for example.

However, there is a need for automatic injection devices to provide injection control in compact device such that the device is easy to handle and discrete for a patient who may wear the device for an extended period of time. Moreover, the elements of the device should be configured for easy replacement of the drug container when the previous container is empty while minimizing the risk of contamination of sterile components.

The present disclosure is direction to an automatic injection device which addresses these needs and the associated problems of the prior art.

SUMMARY

In one aspect, the present disclosure is directed to an automatic injection device. The automatic injection device includes an insertion device, a needle for example, configured to be inserted into a patient and a drug container which contains a pharmaceutical product. The drug container may include a plunger configured to move from a first longitudinal end to a second longitudinal end of the drug container. The automatic injection device also includes a fluid path which fluidly connects the drug container to the insertion needle, and a drive system configured to cause linear movement of the plunger to force the pharmaceutical product into the fluid path. The drive system includes a movable element. The movable element includes a shape memory alloy and is configured to change shape to move the plunger.

In another aspect, the present disclosure is directed to an apparatus for use in an automatic injection device. The apparatus includes a drug container configured to contain a pharmaceutical product and including a first longitudinal end and a second longitudinal end. The apparatus also includes a plunger in the drug container configured to move in a linear direction from the first longitudinal end toward the second longitudinal end. The apparatus additionally includes a movable element formed of a shape memory alloy in the drug container. The movable element is configured to move the plunger in the linear direction based on the shape memory properties of the movable element. In an embodiment, the movable element is a spring body, or a plurality of spring bodies in contact with one another, having shape memory properties.

In yet another aspect, the present disclosure is directed to a cartridge for an automatic injection device. The cartridge includes a space for receiving a drug container which contains a pharmaceutical product, and a drive system including a movable element, the movable element including a spring body, or a plurality of spring bodies, made from a shape memory alloy and being configured to linearly extend or contract based on the shape memory properties of the movable element in the space for receiving the drug container. The drive system also includes a wire, or other holding means, for keeping the movable element in the compressed state until the plunger within the drug container needs moving. In an embodiment, the drive system includes a mechanical restrictor that holds the movable element's force as the movable element travels from the compressed state to the extended state.

An example of movable elements, which includes some of the features that may be incorporated into the device described herein is described in U.S. patent application Ser. No. 15/436,529, which is herein incorporated by reference. However, it should be understood that the device described herein is not limited to the automatic injection device described therein or the exemplary embodiments described below.

DETAILED DESCRIPTION OF THE PREFERRED EMBODIMENTS

Disclosed embodiments pertain to a drive system for an automatic injection device. The drive system provides a force to move an element of the automatic injection device to control delivery of a pharmaceutical product to a patient. For example, the drive system may be configured to control movement of a plunger placed in a drug container. Further movement of the plunger inside the drug container pushes the pharmaceutical product through a fluid path and to an insertion device, for example a needle, which connects to the patient. This controlled movement of the plunger allows for metered delivery of the pharmaceutical product according to desired parameters. In a preferred embodiment the drive system is a passive drive system.

The disclosed drive system includes features which allow for precise control over plunger movement while providing a small form factor which allows the automatic injection device to be compact. The disclosed drive system utilizes a shape memory spring in order to cause movement of the plunger. The shape memory spring may be positioned at least partially or wholly inside of the drug container.

In some embodiments, the shape memory spring is pre-configured with properties which cause the spring to move to assume a "memorized" shape. In some embodiments the memorized shape may be the shape of the spring in the extended state. In returning to this shape, the spring can push the plunger. Because the movement is based on shape memory properties, the force applied to the plunger is substantially constant (as opposed to a conventional spring which applies a variable force). This allows for specific control of the movement of the plunger with a passive drive system. In some embodiments, the shape memory spring is pre-configured with properties that allows for a large maximum travel distance upon extension. This combined with the almost maximal compression of the spring down to a height that is approximately equal to the thickness of the shape memory material, allows for a greater compression ratio that could be obtained from a coiled spring made of similar materials, or than a stainless steel spring made of a similar shape. This change in shape causes movement of the plunger and thus movement of the pharmaceutical product out of the drug container (e.g., and into a patient through a fluid path).

The drive system may also include a holding means, such as a wire for example, which is coupled to the shape memory spring to maintain the shape memory spring in the compressed state, keeping the plunger from moving and keeping the pharmaceutical product from being forced out of the drug container. The holding means can include attachment of a wire to the shape memory spring, but may also include any other means of holding known in the art.

In an embodiment, the drive system may include a mechanical restrictor operatively coupled to the shape memory spring. The mechanical restrictor restricts movement of the pharmaceutical product from the drug container 20 to the fluid path 22 and ultimately into the patient 10 at a proscribed rate. Upon release of the holding means from the shape memory spring, the mechanical restrictor regulates movement of a plunger by regulating movement of the shape memory spring from the compressed state to the expanded state allowing for greater control of the rate of change in shape of the shape memory spring from the compressed state to the extended state. The mechanical restrictor may include any means of controlling the change in shape of a spring from the compressed state to the extended state. In a non-limiting embodiment, the mechanical restrictor 90 may include a mechanical unit. In another embodiment, the mechanical restrictor 90 may include both a mechanical unit and a small electrical unit that may exert a minimal amount of energy for regulating movement of the plunger and release of the fluid at a proscribed pace. For example, in one embodiment, the mechanical restrictor 90 may include a ratchet mechanism that releases potential energy from the potential energy source at a certain pace and exerts a small fraction of energy in order to stop the mechanism in a required pace. The ratchet may be stopped and released by a small electrical unit such as a solenoid or a different actuator. In addition, in another embodiment, the regulator may control the flow between the needle and the fluid path by periodically obstructing fluid flow.

Figure 1:
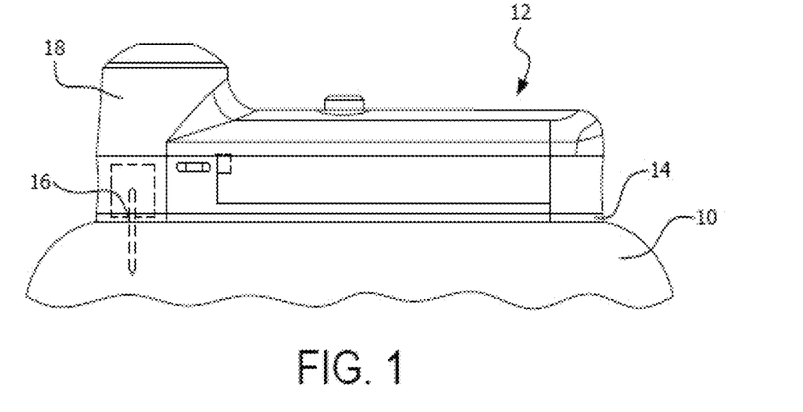
FIG. 1 is a side view illustration of an exemplary automatic injection device positioned on a patient.

FIG. 1 is a depiction of an exemplary embodiment of an automatic injection device 12 on a patient 10. The patient 10 is not limited and can be any organism which may receive an injection. The device 12 is configured to deliver a pharmaceutical product to the patient 10 automatically. This means that the device 12 is controlling the injection in some way such that the system differs from other injection systems where manual input alone causes the injection (i.e., a conventional syringe and needle system or other available systems). The automatic aspect of the device 12 may additionally or alternatively relate to the duration of the injection, controlled injection intervals, a delay between input and injection, etc.

The device 12 includes a base 14 that contacts the patient's skin. The device 12 includes an insertion needle 16 which enters the patient 10 to deliver a pharmaceutical product, such as insulin, to the patient. An example of an automatic injection device which includes many of the features that may be incorporated into the device 12 is described in WO 2017/007952, which is herein incorporated by reference. However, it should be understood that the device 12 is not limited to the automatic injection device described therein or the exemplary embodiments described below. An automatic injection device consistent with this disclosure may include some of the features described herein but is not limited thereto. For example, a disclosed automatic injection device may resemble a syringe and needle system or other injection system which is adapted for automatic injections via the features described herein.

Figure 2:
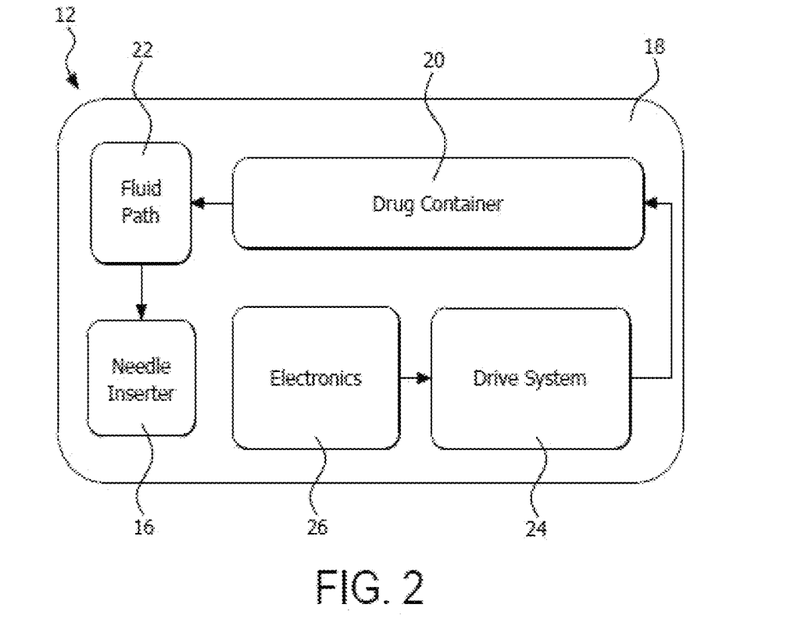
FIG. 2 is a schematic illustration of the components of an automatic injection device consistent with disclosed embodiments.

FIG. 2 is a schematic illustration of the automatic injection device 12 and the basic features of the device 12 which facilitate automatic injections of a pharmaceutical product into the patient 10. The device 12 preferably includes a housing 18 which holds at least some of the features of the device 12. In addition to the insertion needle 16, these features preferably include a drug container 20, a fluid path 22, a drive system 24, and potential energy source 26. These features work in conjunction with each other to automatically deliver a pharmaceutical product to the patient 10 according to desired parameters. In an embodiment, the drive system 24 is a passive system. In an embodiment, the potential energy source 26 may be in the form of electronics configured to provide energy input to elements potentially found in automated injection devices. Non-limiting examples of such elements are light-emitting diode (LED) lights, sensors and indicators, and components configured to provide connectivity to other devices. In another embodiment, the mechanical restrictor 90 may include electronics 26.

The drug container 20 is a containing element which supplies the pharmaceutical product. The drug container 20 may be a vial, syringe, or the like and includes a space for containing the pharmaceutical product, which is not limited to a particular substance. The pharmaceutical product may be any substance which is considered one or more of a drug, biologic, medication, or placebo, for example. The drug container 20 is preferably a hollow cylindrical tube which receives the pharmaceutical product. However, it should be understood that other configurations are possible.

In the device 12, the drug container 20 is fluidly connected to the insertion needle 16 by the fluid path 22. The fluid path 22 may be a physical connecting channel which serves as a conduit for delivering the pharmaceutical product from the drug container 20 to the insertion needle 16 and ultimately into the patient 10. The fluid path 22 may include additional structure, including actuating mechanisms which initiate delivery of the pharmaceutical product and/or control mechanisms which meter an amount of product which is delivered to the patient 10 at any particular time. The fluid path 22 may include an element or mechanism which is configured to establish the connecting channel, such as a puncturing needle or the like. The fluid path 22 may be associated with a start button or control switch or even the electronics 26 which control an element of the fluid path 22 (e.g., a valve) in order to start or stop the delivery of the pharmaceutical product. It should be understood, however, that the fluid path 22 may be a passive system component in at least some embodiments.

The drive system 24 provides the automatic aspect of the injections via device 12. For example, the drive system 24 is a mechanical system which physically moves an element of the device 12 to move the pharmaceutical product from the drug container 20 to into the fluid path 22 and ultimately into the patient 10. For example, the drive system 24 may be configured to move a plunger positioned inside the drug container 20 to force the pharmaceutical product out of the drug container 20. The drive system 24 includes a shape memory spring 44 formed from a shape memory alloy, as will be described in more detail herein.

Figure 3:
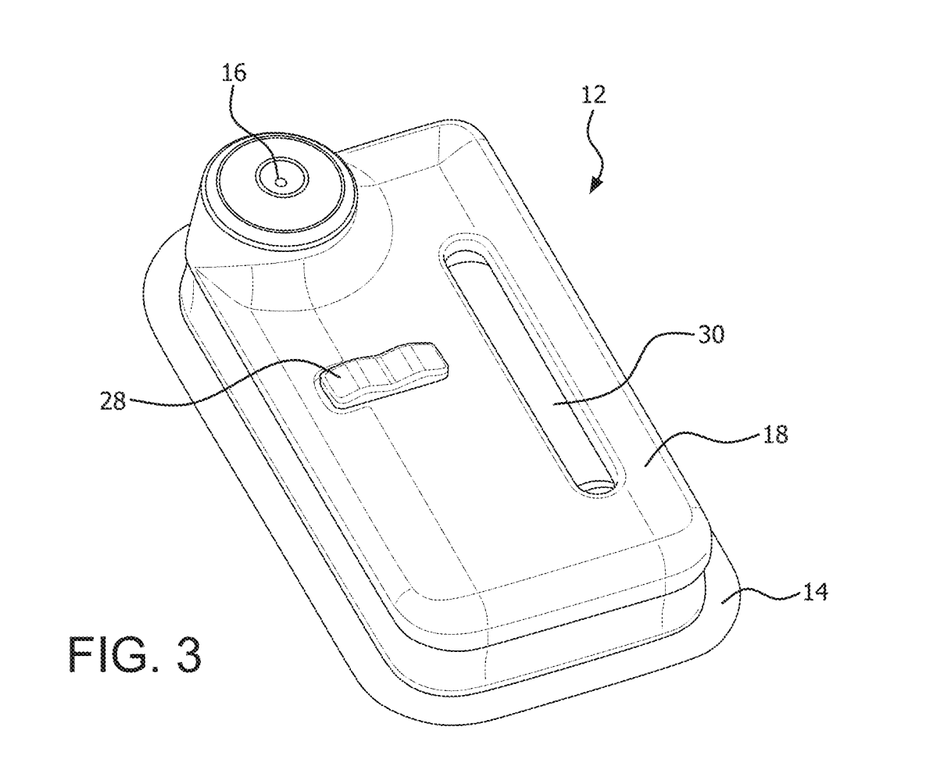
FIG. 3 is a perspective view of a top side of the automatic injection device.
Figure 4:
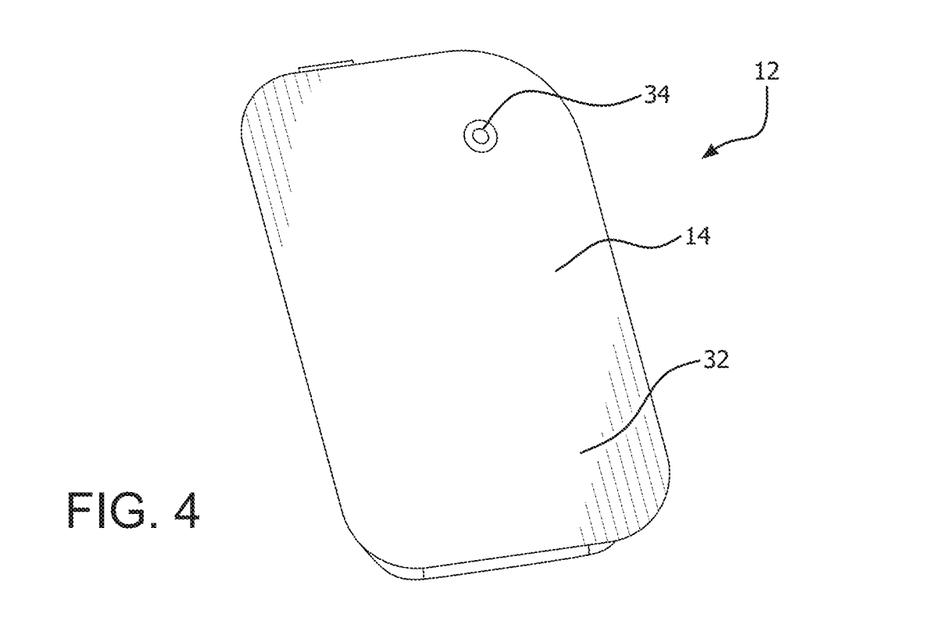
FIG. 4 is a perspective view of a bottom side of the automatic injection device.

FIGS. 3 and 4 further illustrate an exemplary embodiment of the automatic injection system 12. FIG. 3 illustrates a first side of the device 12, including the housing 18 which rests on top of the base 14. The housing 18 is illustrated as being rectangular, but can include any shape. The housing 18 may include optional features such as at least one control switch 28 which provides an input signal to the electronics 26 or other elements of the device 12, and/or a window 30 which provides a view of the drug container 20 and thus the current fluid level.

FIG. 4 illustrates a second side of the device 12 including a bottom surface of the base 14. The bottom surface 32 includes an opening 34 for receiving the insertion needle 16 therethrough. In use, the device 12 is placed against the patient 10 with the bottom surface 32 of the base 14 against the skin. An injection needle extends through the opening 34 and into the patient 10 to deliver the pharmaceutical product. The bottom surface 32 may include an adhesive material thereon to adhere the device 12 to the patient 10 for either a short or long period of time, depending on the particular use of the device 12.

Figure 5:
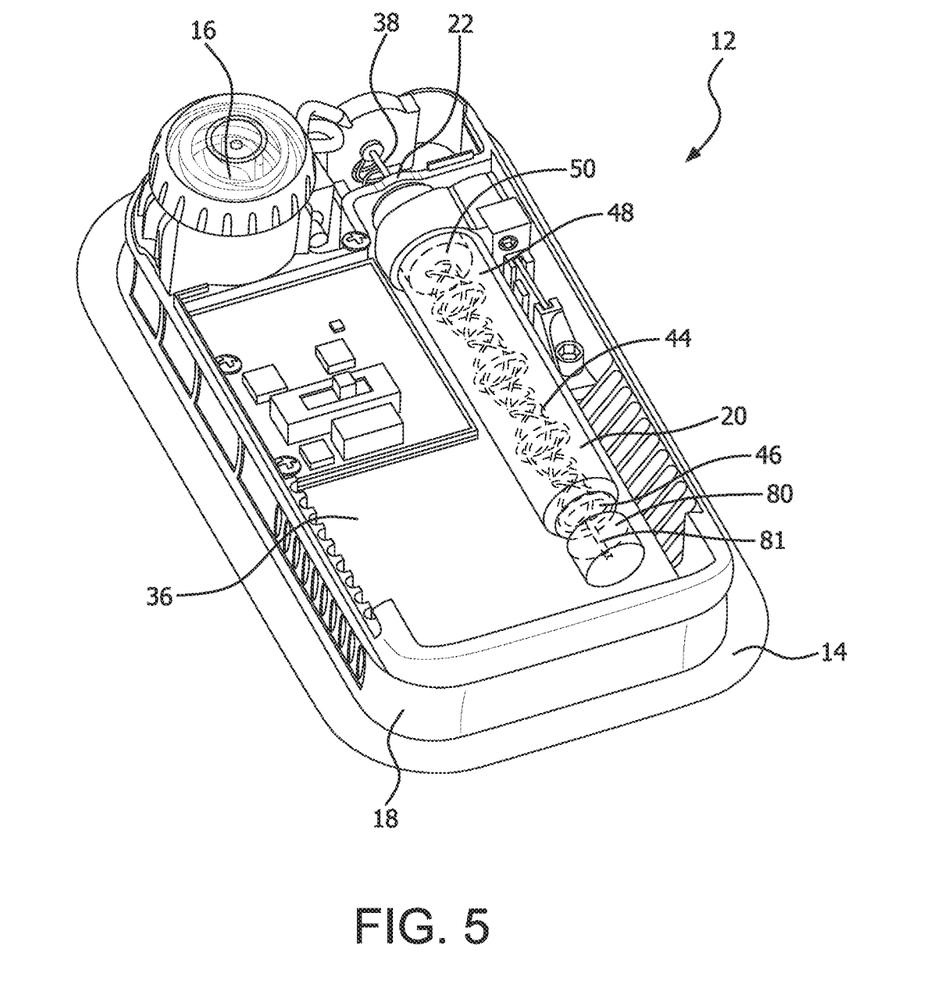
FIG. 5 is a perspective view of the internal components according to an embodiment of the automatic injection device.

FIG. 5 illustrates the device 12 with the top portion of the housing 18 removed such that the internal features are shown in an enclosed space 36 formed by a lower portion of the housing 18 and the base 14. The device 12 includes exemplary embodiments of the insertion needle 16, the drug container 20, the fluid path 22, and a holding means 80. The holding means 80 may include a wire 81 or any other mechanism known in the art to prevent a spring body from moving. The enclosed space 36 houses at least the drug container 20, shape memory spring 44, and holding means 80 including wire 81. In an embodiment the mechanical restrictor 90 as described in the drawings and hereinafter may be included in the enclosed space 36 (not depicted).

The fluid path 22 in this embodiment includes a connector 38 which physically connects to the drug container 20 to establish a connection channel between the interior of the drug container 20 and the insertion needle 16. In the illustrated embodiment, the insertion needle 16 is positioned perpendicular to the drug container 20 such that the path of the pharmaceutical product is to travel out of the drug container 20 and laterally into the area of the insertion needle 16 via the fluid path 22. The pharmaceutical product subsequently travels vertically downward through the insertion needle 16 and into the patient 10. This configuration is exemplary, however, and disclosed embodiments are not limited thereto. In other embodiments, the insertion needle 16 may be aligned in the same direction as the drug container 20 and/or the fluid path 22.

Figure 6:
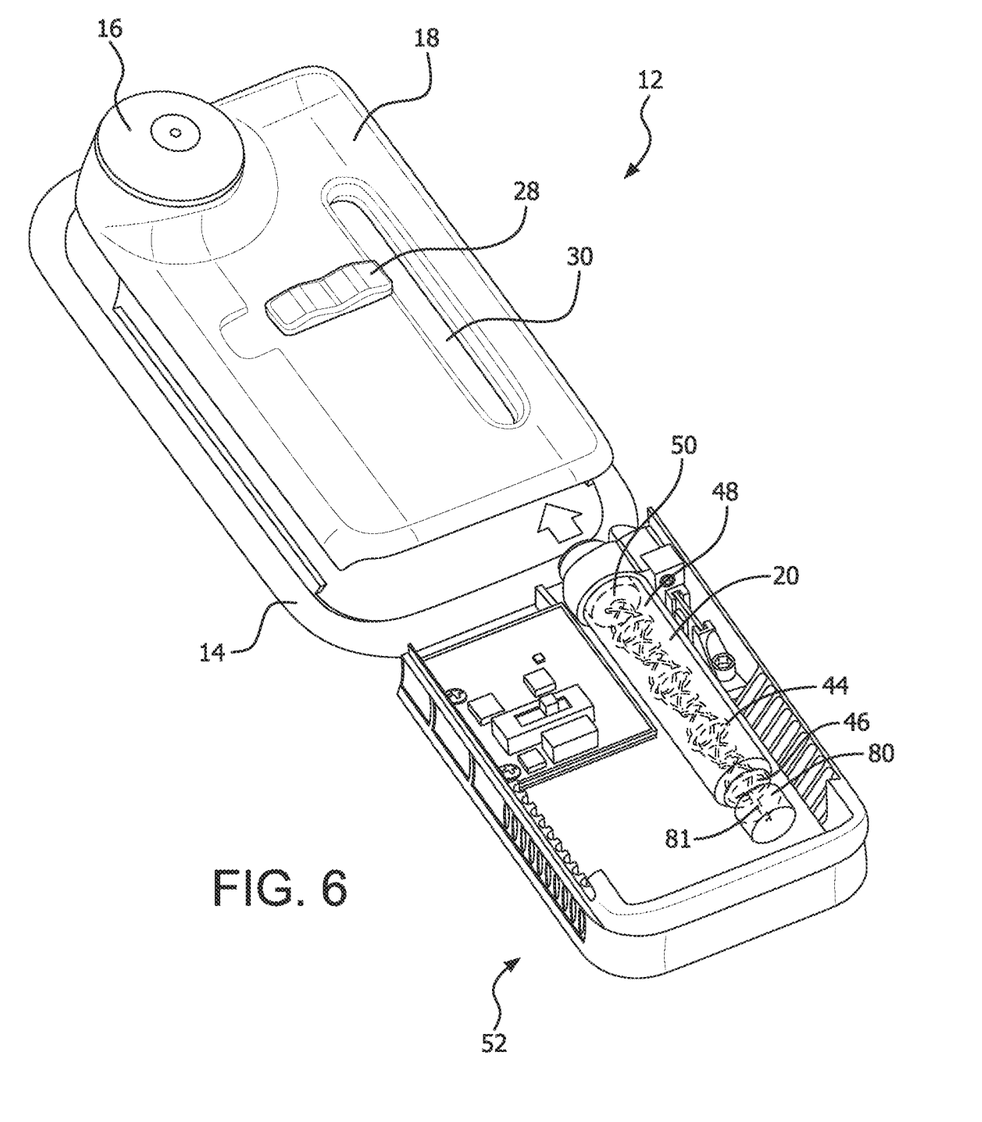
FIG. 6 is a perspective view of a separated housing and cartridge according to an embodiment of the automatic injection device.

FIG. 6 illustrates an embodiment of the device 12 which includes drug container 20, drive system 24, and holding means 80 as a removable cartridge 52 relative to the housing 18, the fluid path 22, and the insertion needle 16. The drug container 20 is removable from the cartridge 52 for replacement after use. This configuration allows for insertion and replacement of the drug container 20 and helps with separating sterile components (e.g., the housing 18 and the drug container 20) from non-sterile components (e.g., the cartridge 52).

Shape memory alloys, such as alloys of copper-nickel-aluminum or nickel-titanium, are metallic materials which change in shape when an input parameter is applied, such as heat or electric current. These changes occur due to a transition in the crystalline structure of the material, such as conversion between austenite and martensite. Shape memory alloys may include different shape configurations which occur under different conditions. For example, a shape memory alloy may have a low temperature shape and a high temperature shape. Application of heat (or current) to a shape memory alloy in its low temperature shape causes the material to assume its high temperature shape. In some materials, subsequent lowering of the temperature (or removal of current) of the material causes the shape memory alloy to return to the low temperature shape.

The shape memory alloy may elongate when changing between the different "memorized" shapes. With the spring body 44 of the present disclosure being formed from a shape memory alloy, a change in temperature and/or current will cause the spring body 44 to longitudinally extend or retract from its current position. Similarly, a change in shape (e.g., compression of a spring) may also cause the shape memory alloy to return to a "memorized" shape (e.g., an extended shape). This movement may appear like and be influenced by a spring-biasing properties, but includes shape memory properties which contribute to the change. This linear movement of the spring body 44 (either through passive or driven change in shape) can be used to force a pharmaceutical product out of the drug container 20, as will be further described.

In embodiments of the device 12, the movable element is preferably the spring body 44 with shape memory properties. It may be formed from a flat sheet of a shape memory alloy material having a special geometry, which is described in greater detail herein. The flat sheet of the shape memory alloy material is heated to, or above a critical temperature characteristic of the shape memory alloy material. At or above this critical temperature, the spring body 44 changes shape to the extended position. This spring body 44 in this extended position is rapidly cooled, and at the lower temperature, or temperatures less than the critical temperature of the shape memory alloy, the spring body 44 remains in the extended state. In a non-limiting embodiment, the temperature used to heat the flat sheet of a shape memory alloy having a special geometry is 500° C. Other temperatures could be used, but should remain greater, or significantly greater, than the temperature at which the spring body 44 will operate. For example, for use in human patients, this critical temperature must be greater, or significantly greater than physiological human body temperature With the spring body 44 defaulting to the extended state at room temperature, or in vivo temperatures for use in patients, the spring body must be restrained in order to remain in the compressed state. In the device described herein, this can be done using holding means 80 having a wire 81 for example to maintain the spring body 44 in the contracted state.

The spring body 44 may also include biasing properties. In these embodiments, the spring body 44 is preferably formed such that it changes shape by extending (similar to a conventional spring). However, because the spring body 44 is a shape memory alloy formed according to selected conditions, the spring body 44 will apply a substantially constant force as it extends (unlike a conventional spring which applies a variable force as its length changes).

Figure 7:
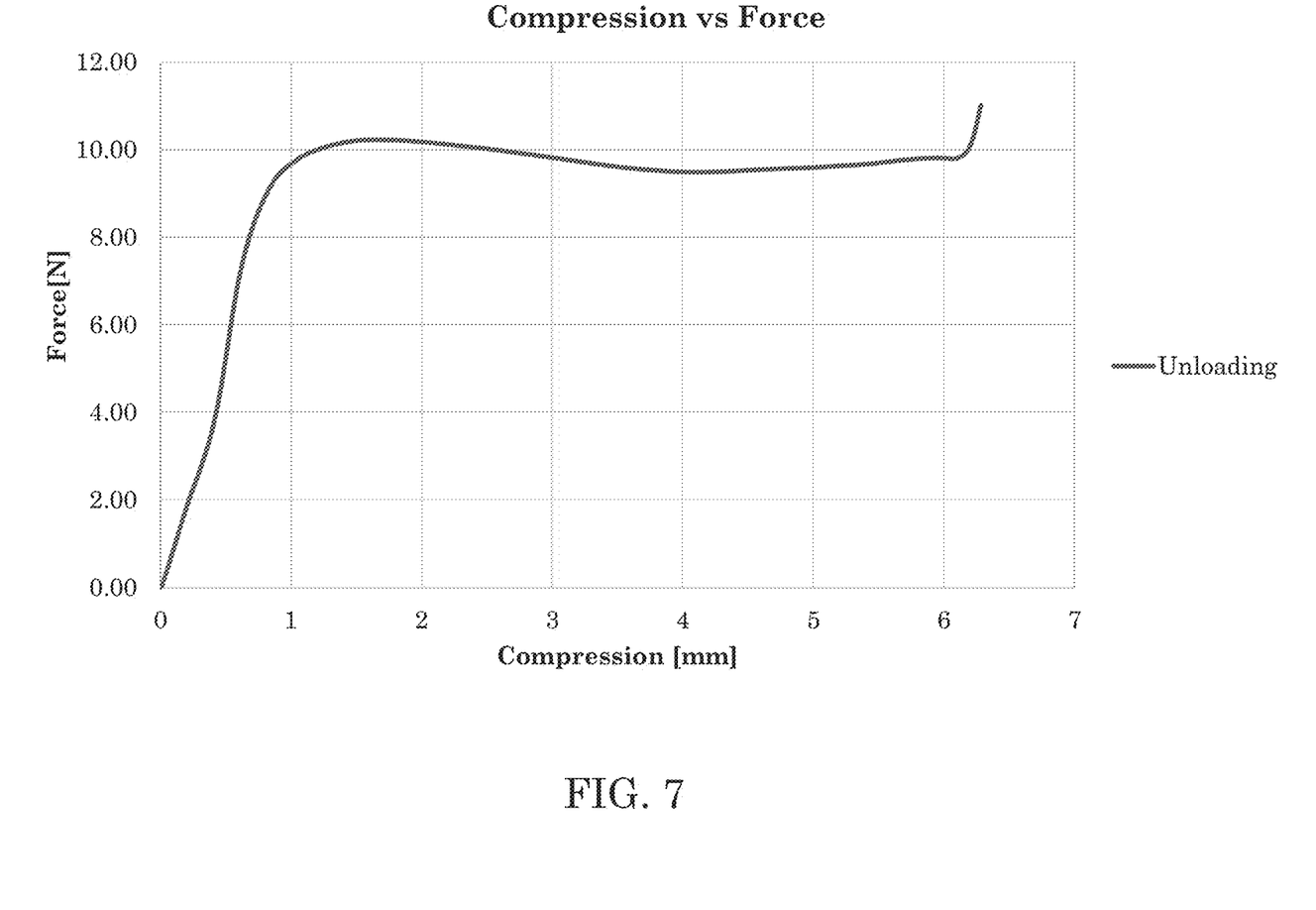
FIG. 7 is graphical representation of a compression versus force diagram of a spring body moving from a compressed state to an extended state.

FIG. 7 illustrates the force versus compression relationship during unloading of an exemplary spring body 44. As illustrated from the graph, upon returning to the extended position from the compressed position, the force generated by the spring body 44 is relatively constant over the majority of the extension. In the example, once the spring body extends to approximately 0.8-0.9 mm, the force generated by the spring body 44 remains constant until the spring is fully extended at approximately 6 mm. This relationship is observed using other spring bodies 44 formed as described herein, and is not limited to this single example.

Figure 8A:
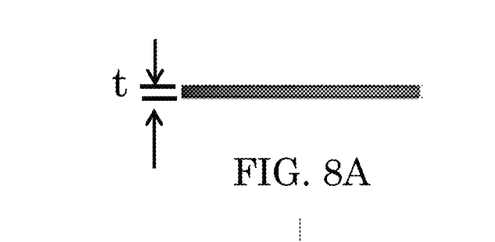
FIG. 8A is a cross-sectional view of an embodiment of the spring body before activation.
Figure 8B:
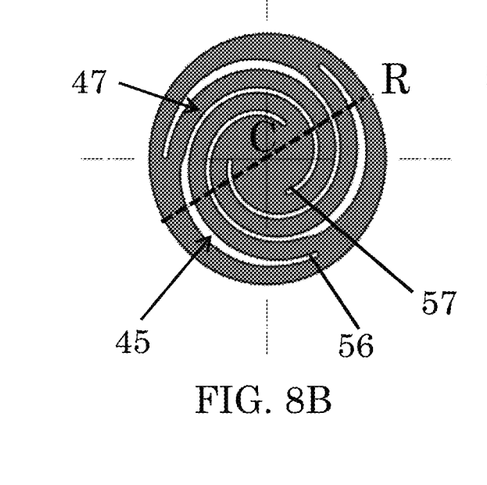
FIG. 8B is a top view of an embodiment of the spring body before activation.

FIGS. 8A and 8B illustrates an embodiment, the special geometry of the flat sheet of a shape memory alloy material prior to the heating or "activation" step. In this embodiment, a plurality of openings 45 and a plurality of arms 47 that are interconnected and form the borders of the plurality of openings 45. In an embodiment, each opening of the plurality openings 45 begins at a first end opening 56 proximal to an outer edge of the spring body and turns inward along a non-linear pathway along a length of the opening to a second end opening 57 proximal to a center C of the spring body 44. In an embodiment, each opening of the plurality of openings overlaps 45 with itself along an exemplary reference line R of the spring body 44 extending through the center C to opposing surfaces of the outer edge.

In an embodiment, the first end opening 56 of each opening of the plurality of openings 45 are angularly staggered relatively along the outer edge the spring body 44. In this or another embodiment, the second end opening 57 of each opening of the plurality of openings 45 are angularly staggered relatively around the center C of the spring body 44. In a non-limiting embodiment, a width of each opening of the plurality of openings 45 is not constant along its length. The width of the opening may be more narrow proximal to either the first end opening 56 or the second end opening 57 and wider towards the middle of the opening 45 along its length.

As illustrated in FIGS. 8A and 8B the spring body 44 is relatively planar in the compressed state, comprising a first planar surface and a second planar surface. The thickness t of the outer edge extends between the first planar surface and the second planar surface and in the "non-activated" state (FIG. 8A) represents the thickness of the shape memory alloy sheet used to form the spring body 44.

Figure 8C:
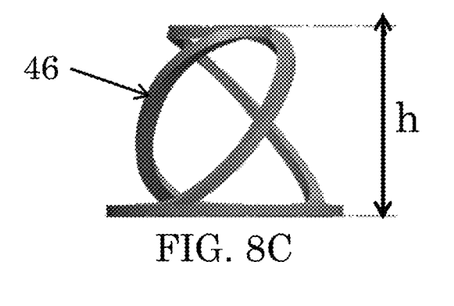
FIG. 8C is a cross-sectional view of an embodiment of the spring body following activation.
Figure 8D:
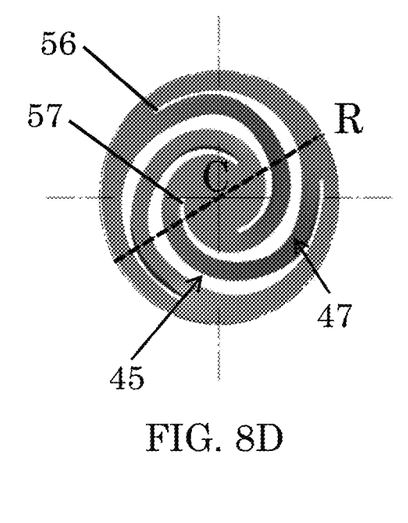
FIG. 8D is a top view of an embodiment of the spring body following activation.

FIGS. 8C and 8D represent the spring alloy 44 following "activation," or heating to at least a critical temperature defined herein, followed by rapid cooling. As illustrated in FIG. 8C, the spring body 44 is no longer planar, and is in an extended state. FIG. 8D, also illustrates changes in the configuration of the openings 45 and arms 47; however, the same general pattern is still observed.

Figure 8E:
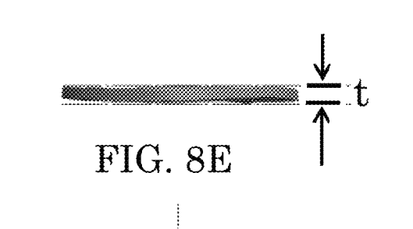
FIG. 8E is a cross-sectional view of an embodiment of the spring body following activation in the compressed state.
Figure 8F:
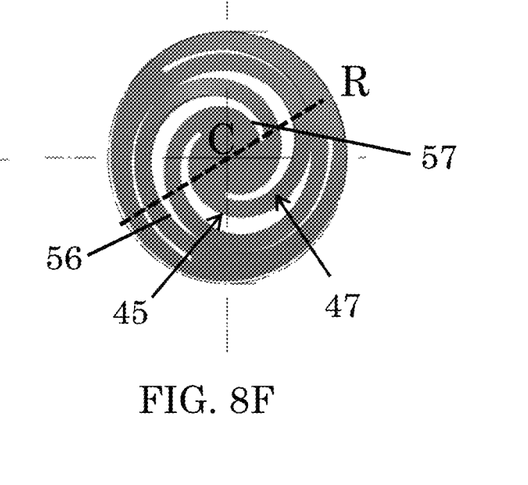
FIG. 8F is a top view of an embodiment of the spring body following activation in the compressed state.

FIGS. 8E and 8F represent the spring alloy 44 following "activation," or heating to at least a critical temperature defined herein, followed by rapid cooling, but the spring body depicted in these figures is in the compressed state. In these examples, the thickness t of the outer edge is still substantially planar and is approximately the thickness of the shape memory alloy sheet used to form the spring body 44. In an embodiment, the thickness may have increased slightly from its original dimensions; however, relative to the increase in the height h of the spring body in the extended state, this remains minimal. FIG. 8F, also illustrates changes in the configuration of the openings 45 and arms 47; however, the same general pattern is still observed.

In a non-limiting example, the diameter of the planar spring body before "activation" is 9.1 mm and the thickness t of the shape memory alloy sheet used to form the spring body 44 is 0.4 mm. Following "activation," the diameter is approximately the same; however, the height of the spring body is 6.8 mm. This represents a compression ratio of 17, which is higher of most typical stainless steel springs and other coiled springs.

In one example, following "activation" of the spring body 44 in which the spring body is shaped or extended to a relatively long length, the spring body is shaped or compressed to a relatively short length prior to use of the spring body 44 in the device 12. During formation of the device at temperatures below the critical temperature described herein, the spring body 44 is assembled into the drug container 20 and connected to a holding means 80 through a wire 81 or any other means known in the art to hold a spring in a compressed state. Following removal of the holding means 80, the spring body 44 is configured to extend into a longer effective length, thereby pushing anything in contact with a moving end of the spring body 44. This change may occur under selected conditions, such as when the spring body 44 is compressed and restrained by holding means at room temperature followed by removal of the holding means 80 and wire 81.

In an embodiment a mechanical restrictor 90, operatively coupled to the spring body 44 may act on the spring body 44 following release of the spring body 44 from holding means 80 and wire 81. The mechanical restrictor restricts movement of the pharmaceutical product from the drug container 20 to the fluid path 22 and ultimately into the patient 10 at a proscribed rate. Upon release of the holding means from the spring body 44, the mechanical restrictor regulates movement of a plunger by regulating movement of the spring body 44 from the compressed state to the expanded state allowing for greater control of the rate of change in shape of the shape memory spring from the compressed state to the extended state. The mechanical restrictor may include any means of controlling the change in shape of a spring from the compressed state to the extended state. In a non-limiting embodiment described in the foregoing, the mechanical restrictor 90 may include a mechanical unit. In another embodiment, the mechanical restrictor 90 may include both a mechanical unit and a small electrical unit that may exert a minimal amount of energy for regulating movement of the plunger and release of the fluid at a proscribed pace.

The drug container 20 includes a first longitudinal end 46, a second longitudinal end 48, and a plunger 50. In an exemplary embodiment, the first longitudinal end 46 is adjacent to the holding means 80 and the second longitudinal end is positioned adjacent to the fluid path 22. The plunger 50 is positioned inside of the drug container 20 and is configured to move the pharmaceutical product out of the drug container 20 via movement thereof. The spring body 44 is configured to move the plunger 50. The plunger 50 is preferably sized to create a sealed arrangement inside of the drug container 20, much like a typical syringe plunger. The plunger 50 is disc-shaped or otherwise shaped to match the drug container 20.

Figure 9:
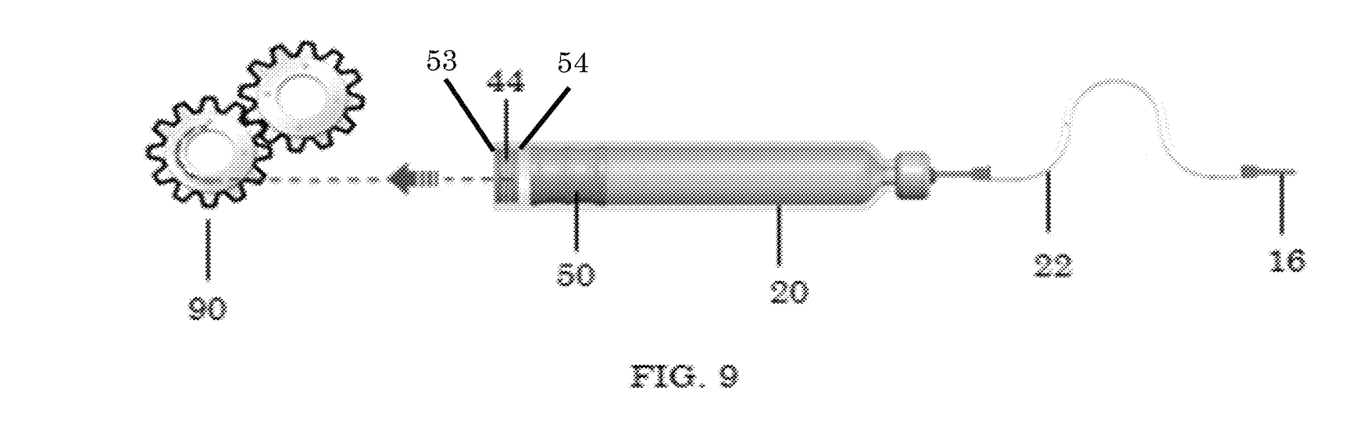
FIG. 9 is a side view of the drive system including the spring body in the compressed state.
Figure 10:
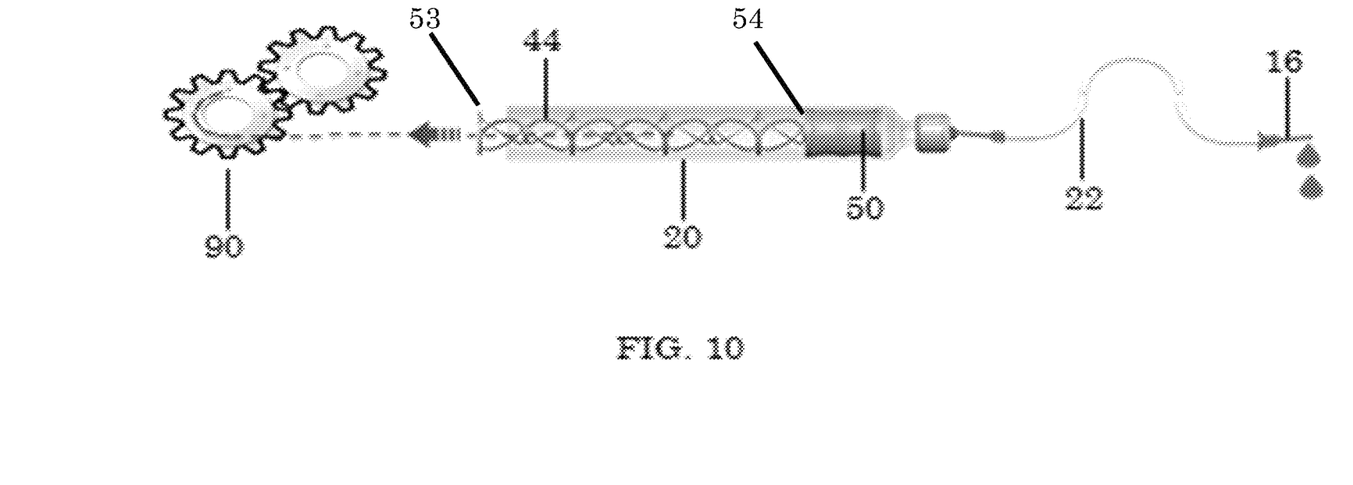
FIG. 10 is a side view of the drive system including the spring body in the extended state.

FIGS. 9 and 10 illustrate the function of the drive system 24 in relation to the drug container 20 according to an embodiment in which the spring body 44 is positioned inside of the drug container 20. As illustrated in FIG. 9, in the compressed state a first end 53 of the spring body 44 is positioned at the first longitudinal end 46 of the drug container 20 and a second end 54 of the spring body 44 is in contact with the plunger 50. The holding means 80 or wire 81 are not depicted in this figure, but are understood to be present as depicted in earlier figures. In FIG. 9, the holding means 80 or wire 81 would be engaged with the spring body 44, keeping the spring body in the compressed state. As illustrated in FIG. 10, in the extended state the second end 54 moves in a linear direction towards the second longitudinal end 48 of the spring body 44. In embodiments in which the holding means 80 or wire 81 are uncoupled from the spring body 44, the spring body 44 is preferably pre-configured to move to an extended position as shown in FIG. 10, in a manner similar to a conventional spring. However, because the spring body 44 is a shape memory alloy, the extension is not merely a result of a spring force, but also due to shape memory properties which cause the spring body 44 to change back to its extended shape. Because the spring body 44 is a shape memory alloy having a special geometry as described herein, the compression ratio is greater than for a coil spring, which can be attributed at least in part to the small thickness of the planar spring body in the compressed state, as well as the great degree of length that the spring body 44 attains in the extended states.

Further, the shape-returning force allows the spring body 44 to provide a constant force which is applied to the plunger 50. In this way, the spring body 44 can be configured to move the plunger 50 at a predetermined, constant rate to force the pharmaceutical product out of the drug container 20.

In a preferred embodiment, the cross-sectional shape of the spring body 44 in the compressed form is a planar disc as depicted in FIGS. 8B, 8D, and 8F. However, other cross-sectional shapes of the spring body 44 are possible, including but not limited to square, rectangles, hexagons, octagons, and others. In each of these embodiments, the spring body 44 may be formed from a shape configured to extend and/or retract upon receipt of an input parameter from the driving element 40, such as release of holding means 80 or wire 81. In general, the spring body 44 is configured to change in shape to linearly move the plunger 50. The change includes a change in shape due to shape memory properties. In some instances, the change in shape may be further controlled by a mechanical restrictor 90.

FIGS. 9 and 10 further illustrate the organization of the spring body 44 within the drug container 20. In an embodiment a single spring body 44 unit may be included in the drug container 20. In other embodiments, for example such as one depicted in FIGS. 9 and 10, a plurality of individual spring body 44 units may be included within the drug container 20. The number of these spring body 44 units may be determined based on the height to which each spring body 44 unit can be extended, but also on the length of the drug container 20. Typically, a longer drug container would require a plurality of spring body 44 units while a small container may only require a single spring body 44 unit. In a preferred embodiment, the spring body 44 units are arrange in opposition, meaning the head 77 of one spring body 44 unit touches the head 77 of another forming a pair. This pair may be adjacent to another pair, and the point of contact between the pairs would be formed by tail 78 of one spring body 44 unit of a pair touching the tail of another spring body 44 unit of another pair. This description is for illustrative purposes only and the spring body 44 units are not limited to exist as pairs.

Consistent with disclosed embodiments, the drive system 24 causes linear movement of the plunger 50 by changing the shape of the spring body 44, which is formed of a shape memory alloy. In some embodiments, the spring body 44 moves the plunger 50 (e.g., the spring 44 is arranged inside the drug container 20) based on properties of the shape memory alloy material and the special geometry of the spring body 44. In other embodiments, the spring body 44 moves the plunger 50 based on properties of the shape memory alloy material and the special geometry of the spring body 44, and also based on the control exerted by the mechanical restrictor 90.

Some or all of the described components may be omitted and/or substituted by similar components. For example, the mechanical restrictor 90 may be removed.

The drug container 20 may be a single-use component which is replaced after use. For example, an empty drug container 20 may be removed from the cartridge 52 (FIG. 6) and replaced with a full drug container 20. Each drug container 20 may be manufactured for use with a selected device configuration. For example, each drug container 20 may include the spring body 44 already inside the drug container 20. In other embodiments, the spring body 44 may be added to the drug container 20 before, during, or after loading into the cartridge 52.

The spring body 44 may be a reusable component which is secured in place on the device 12. After an empty drug container 20 is removed, the extended spring body 44 body may be reset by compressing it and applying another holding means 80 or wire 81, which maintains the compressed shape of the spring body 44.

In an assembly process, the drug container 20 may be slid into contact with the first end 54 of the spring body 44 and then the cartridge 52 inserted into the housing 18 of the device 12. It should be understood, however, that this is an exemplary configuration and that other embodiments are possible. For example, the housing 18 may be a single unit which includes an opening for receiving the drug container 20.

The disclosed features are applicable to any injection device in order to cause movement of a plunger. This disclosed configurations are especially applicable to an automatic injection device where a driving element is present. The feature of the movable element including a shape memory alloy provides a large amount of force in a small form factor which enables a compact device.

Having thus described the presently preferred embodiments in detail, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiments and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

What is claimed is:

1. An apparatus for use in an automatic injection device, the apparatus comprising:
    a drug container configured to include a pharmaceutical product and including a first longitudinal end and a second longitudinal end with a drug flow opening;
    a plunger that fits within the drug container;
    a movable element made of a shape memory alloy, having a first end and a second end, located within the drug container, where the second end of the movable element abuts the plunger and urges the plunger toward the second longitudinal end of the drug container by expanding based on shape memory properties of the movable element; and
    a drive system comprising the movable element, a mechanical restrictor operatively coupled to the movable element, and a holding means adjacent to the first longitudinal end of the drug container, wherein
    the movable element is comprised of a spring body,
    the spring body comprises a plurality of openings,
    the spring body comprises a plurality of interconnected arms formed of the shape memory alloy, having an upper surface and a lower surface,
    the upper surface and the lower surface of each arm of the plurality of interconnected arms is substantially free from contact with the upper surface and the lower surface of all arms of the plurality of interconnected arms in both an extended state of the spring body and in a compressed state of the spring body,
    the spring body is located within the drug container in both the extended state and the compressed state,
    the holding means comprises a wire that couples with the movable element and holds the movable element in the compressed state preventing the movable element from moving to the extended state,
    the mechanical restrictor comprises a ratchet mechanism that further regulates movement of the plunger from the compressed state to the extended state at a proscribed rate upon release of the holding means from the movable element, and
    the drive system provides a small form factor which allows the automatic injection device to be compact.

2. The apparatus for use in the automatic injection device of claim 1, wherein the shape memory properties include the spring body returning to the extended state after being compressed.

3. The apparatus for use in the automatic injection device of claim 1, wherein the spring body is configured to move from the compressed state to the extended state under a substantially constant force.

4. The apparatus for use in the automatic injection device of claim 1, wherein the spring body moves the plunger in a linear direction from the first longitudinal end towards the second longitudinal end in the extended state.

5. The apparatus for use in the automatic injection device of claim 4, wherein:
    each opening of the plurality of openings begins at a first end opening proximal to an outer edge of the spring body and turns inward along a non-linear pathway along a length of each opening of the plurality of openings to a second end opening proximal to a center of the spring body, and
    each opening of the plurality of openings overlaps with itself along a reference line of the spring body extending through the center to opposing surfaces of the outer edge.

6. The apparatus for use in the automatic injection device of claim 5, wherein:
    the first ends of each opening of the plurality of openings are angularly staggered relatively along the outer edge,
    the second ends of each opening of the plurality of openings are angularly staggered relatively around the center.

7. The apparatus for use in the automatic injection device of claim 5, wherein in the compressed state the plurality of arms borders the plurality of openings.

8. The apparatus for use in the automatic injection device of claim 5, wherein in the compressed state, the spring body comprises a first planar surface, a second planar surface, and a thickness of the outer edge extending between the first planar surface and the second planar surface.

9. The apparatus for use in the automatic injection device of claim 5, wherein the spring body in the compressed state has a disc profile.

10. The apparatus for use in the automatic injection device of claim 5, wherein the spring body has a greater compression ratio than a coiled-shaped spring body made of the shape memory alloy.

11. The apparatus for use in the automatic injection device of claim 5, wherein a width of each opening of the plurality of openings is not constant along the length.

12. The apparatus for use in the automatic injection device of claim 1, wherein the shape memory alloy has a first shape configuration under a first input condition and a second shape configuration under a second input condition, such that the second input condition drives the spring body to be in the extended state.

13. The apparatus for use in the automatic injection device of claim 1, wherein the spring body is formed from a single spring body unit or a plurality of spring body units.

14. The apparatus for use in the automatic injection device of claim 1, wherein the mechanical restrictor further comprises an electrical unit, and the electrical unit exerts energy for regulating movement of the plunger.

15. A cartridge for an automatic injection device, comprising:
    a space for receiving a drug container configured to include a pharmaceutical product and comprising a plunger that fits within the drug container; and
    a movable element made of a shape memory alloy, having a first end and a second end, located within the drug container having a first longitudinal end and a second longitudinal end, where the second end of the movable element abuts the plunger and urges the plunger toward the second longitudinal end of the drug container by expanding based on shape memory properties of the movable element; and
    a drive system comprising the movable element, a mechanical restrictor operatively coupled to the movable element, and a holding means adjacent to the first longitudinal end of the drug container, wherein the movable element is comprised of a spring body, the spring body comprises a plurality of openings, the spring body comprises a plurality of interconnected arms formed of the shape memory alloy, having an upper surface and a lower surface, the upper surface and the lower surface of each arm of the plurality of interconnected arms is substantially free from contact with the upper surface and the lower surface of all arms of the plurality of interconnected arms in both an extended state of the spring body and in a compressed state of the spring body, the spring body is located within the drug container in both the extended state and the compressed state, the holding means comprises a wire that couples with the movable element and holds the movable element in the compressed state preventing the movable element from moving to the extended state, the mechanical restrictor comprises a ratchet mechanism that further regulates movement of the plunger from the compressed state to the extended state at a proscribed rate upon release of the holding means from the movable element, and the drive system provides a small form factor which allows the automatic injection device to be compact.

16. The cartridge of claim 15, wherein the plunger is configured to move in a linear direction from the first longitudinal end towards the second longitudinal end of the drug container in response to the spring body moving into the extended state.

17. An automatic injection device, comprising:

an insertion device configured to be inserted into a patient;

a drug container configured to include a pharmaceutical product and including a first longitudinal end and a second longitudinal end with a drug flow opening, a plunger that fits within the drug container;

a fluid path which fluidly connects the drug container to an insertion device; and a movable element made of a shape memory alloy, having a first end and a second end, located within the drug container, where the second end of the movable element abuts the plunger and urges the plunger toward the second longitudinal end of the drug container by expanding based on shape memory properties of the movable element; and a drive system comprising the movable element, a mechanical restrictor operatively coupled to the movable element, and a holding means adjacent to the first longitudinal end of the drug container, wherein the movable element is comprised of a spring body, the spring body comprises a plurality of openings, the spring body comprises a plurality of interconnected arms formed of the shape memory alloy, having an upper surface and a lower surface, the upper surface and the lower surface of each arm of the plurality of interconnected arms is substantially free from contact with the upper surface and the lower surface of all arms of the plurality of interconnected arms in both an extended state of the spring body and in a compressed state of the spring body, the spring body is located within the drug container in both the extended state and the compressed state, the holding means comprises a wire that couples with the movable element and holds the movable element in the compressed state preventing the movable element from moving to the extended state, the mechanical restrictor comprises a ratchet mechanism that further regulates movement of the plunger from the compressed state to the extended state at a proscribed rate upon release of the holding means from the movable element, and the drive system provides a small form factor which allows the automatic injection device to be compact.

18. The automatic injection device of claim 17, wherein:

each opening of the plurality of openings begins at a first end opening proximal to an outer edge of the spring body and turns inward along a non-linear pathway along a length of each opening of the plurality of openings to a second end opening proximal to a center of the spring body, each opening of the plurality of openings overlaps with itself along a reference line of the spring body extending through the center point to opposing surfaces of the outer edge, the first ends of each opening of the plurality of openings are angularly staggered relatively along the outer edge, the second ends of each opening of the plurality of openings are angularly staggered relatively around the center, and in the compressed state the plurality of arms borders the plurality of openings.

19. The automatic injection device of claim 17, wherein the spring body in the compressed state has a disc profile.

* * * * *